(12) United States Patent
Keen

(10) Patent No.: US 8,069,055 B2
(45) Date of Patent: Nov. 29, 2011

(54) PREDICTIVE SCHEDULING FOR PROCEDURE MEDICINE

(75) Inventor: Ronald Keen, Shelbourne, VT (US)

(73) Assignee: General Electric Company, Schenectady, NY (US)

( * ) Notice: Subject to any disclaimer, the term of this patent is extended or adjusted under 35 U.S.C. 154(b) by 1257 days.

(21) Appl. No.: 11/352,043

(22) Filed: Feb. 9, 2006

(65) Prior Publication Data

US 2007/0203761 A1    Aug. 30, 2007

(51) Int. Cl.
*G06Q 10/00* (2006.01)
*G06Q 50/00* (2006.01)
(52) U.S. Cl. .............................................. 705/2; 705/3
(58) Field of Classification Search ................ 705/2–3, 705/7
See application file for complete search history.

(56) References Cited

U.S. PATENT DOCUMENTS

| 2003/0009356 | A1* | 1/2003 | Hildebrand et al. | 705/2 |
| 2003/0208382 | A1* | 11/2003 | Westfall | 705/3 |
| 2004/0122719 | A1* | 6/2004 | Sabol et al. | 705/7 |

* cited by examiner

*Primary Examiner* — Robert Morgan
*Assistant Examiner* — Joseph Burgess
(74) *Attorney, Agent, or Firm* — Andrus, Sceales, Starke & Sawall, LLP (57) ABSTRACT

Scheduling techniques are disclosed that employ one or more predictive scheduling classification algorithms configured to exploit historical data of previously scheduled and completed medical procedures. Thus, a new patient that is similarly-situated to previously treated patients can have a medical procedure automatically predicted and scheduled based on historical procedure data associated with those previously treated patients.

22 Claims, 7 Drawing Sheets

PREDICTIVE SCHEDULING FOR PROCEDURE MEDICINE

FIELD OF THE INVENTION

The invention relates to scheduling systems, and more particularly, to predictive automated scheduling of patients for diagnostic and therapeutic procedures for specialties such as radiology and cardiology.

BACKGROUND OF THE INVENTION

Traditional scheduling systems rely on table driven rules or a rules processor to determine the optimal scheduling slot for a healthcare procedure, by matching a patient to resources and a time allotted to perform that procedure. There a number of issues associated with scheduling techniques that rely substantially on rules processors and table driven rules.

For instance, inflexible rules require constant tweaking to maximize resource and people utilization. As such, resources (including people's time) are wasted, thereby resulting in expensive healthcare services. In addition, conventional scheduling techniques require a manual process, where statistical reports are reviewed against usage of resources and people. Such statistical review is after the patient procedure is completed, with manual tweaking of the rules processor to correct for inefficient usage of resources and staff.

Also, typical scheduling systems utilize hard-coded time increments for procedures that can result in the over-booking of resources, which is frustrating for both staff and patients. On the other hand, hard-coded time increments for procedures can also under-book resources, which under-utilize staff and equipment, thereby causing poor return on investment (ROI) for the healthcare provider and unnecessary waiting for emergency or walk-in procedures.

Furthermore, a rules processor typically tracks a limited set of attributes to determine the best usage of resources to patient condition/procedure. The problem here is that rules processors are only as accurate as the rules and information to which they are programmed to respond. Also, a rules processor language may need to be re-compiled and the underlying table driven rules software must be changed, to accommodate changing parameters that drive scheduling engine.

What is needed, therefore, are scheduling techniques that are relatively more flexible and require less user intervention than conventional techniques.

SUMMARY OF THE INVENTION

One embodiment of the present invention is a computer-implemented method for predictively scheduling a patient for procedure medicine. The method includes receiving historical patient-procedure data, and transforming that received historical patient-procedure data into a schema. The method continues with building one or more prediction models using the transformed patient-procedure data stored in the schema. The method continues with predictively scheduling a medical procedure for the patient, based on target patient-procedure data and the one or more prediction models. The one or more prediction models may include, for example, Naive Bayes, logistics regression, neural network, maximum entropy, and/or decision tree prediction models. In response to receiving new historical patient-procedure data, the method may include updating the one or more prediction models. In one particular case, predictively scheduling a medical procedure is preceded by receiving a new scheduling event request, which includes the target patient-procedure data. The target patient-procedure data can be transformed to comply with the schema (e.g., in a similar fashion that the historical patient-procedure data is transformed). In another particular case, predictively scheduling a medical procedure includes processing the target patient-procedure data using the prediction models, determining if procedure predictions by the models satisfy a given threshold, and/or determining if a quorum of predictions agree. The historical patient-procedure data may include actual data from previously completed patient procedures, such as procedure attributes, procedure durations, patient demographics, equipment used, and/or attending personnel.

Another embodiment of the present invention provides a machine-readable medium (e.g., one or more compact disks, diskettes, servers, memory sticks, or hard drives) encoded with instructions, that when executed by one or more processors, cause the processor to carry out a process for predictively scheduling a patient for procedure medicine. This process can be, for example, similar to or a variation of the previously described method.

Another embodiment of the present invention is a system for predictively scheduling a patient for procedure medicine. The system includes a learning module for transforming received historical patient-procedure data into a schema, and building one or more prediction models using the transformed patient-procedure data stored in the schema. The system further includes a classifier module for predictively scheduling a medical procedure for the patient, based on target patient-procedure data and the one or more prediction models. In one particular case, the one or more prediction models include a Naïve Bayes prediction model, logistics regression prediction model, and neural network prediction model. In response to receiving new historical patient-procedure, the learning module may be further configured for updating the one or more prediction models. The classifier module can be further configured for determining if procedure predictions by the models satisfy a given threshold, and determining if a quorum of predictions agree. The system functionality can be implemented, for example, in software (e.g., executable instructions encoded on one or more computer-readable mediums), hardware (e.g., gate level logic or one or more ASICs), firmware (e.g., one or more microcontrollers with I/O capability and embedded routines for carrying out the functionality described herein), or some combination thereof. Many suitable means for implementing embodiments of the present invention will be apparent in light of this disclosure.

The features and advantages described herein are not all-inclusive and, in particular, many additional features and advantages will be apparent to one of ordinary skill in the art in view of the figures and description. Moreover, it should be noted that the language used in the specification has been principally selected for readability and instructional purposes, and not to limit the scope of the inventive subject matter.

DETAILED DESCRIPTION OF THE INVENTION

Scheduling techniques are disclosed that are relatively more flexible and require less user intervention than conventional techniques. One particular embodiment of the present invention is a patient scheduling system that employs a predictive scheduling classification algorithm configured to exploit historical data of previously scheduled and completed medical procedures. Thus, a new patient that is similarly-situated to previously treated patients can have a medical procedure automatically predicted and scheduled based on historical procedure data associated with those previously treated patients.

General Overview

Utilizing historical patient-procedure data collected over time, an optimal set of procedure parameters can be predicted for a new patient procedure to take place within a healthcare institution. The historical data can be used, for example, to predict where the procedure should be performed for the new patient and with what piece of equipment, when the procedure should be performed for the new patient, who should perform the procedure for the new patient, and other procedure details such as body positions for best scan results, contrast agents, and procedure timing factors (e.g., 12 hour fast, then contrast, then wait one-half hour, then scan, then wait two hours, then scan again). The historical patient-procedure data includes actual completed procedure data of previous patients. The data can be stored, for example, in a relational, object-oriented, or other suitable database structure. Manual process review of statistical reporting is eliminated or otherwise minimized, as such reporting automatically occurs in real-time during operation of the predictive scheduling algorithm.

The predictive scheduling (e.g., so as to identify optimal resource utilization and/or patient experience) can be accomplished by using data mining techniques. Data mining is sorting through data to identify patterns and establish relationships. Example data mining parameters include: association (looking for patterns where one event is connected to another event), sequence or path analysis (looking for patterns where one event leads to another later event), classification (looking for new patterns, which may result in a change in the way the data is organized but that is ok), clustering (finding and visually documenting groups of facts not previously known), and forecasting (discovering patterns in data that can lead to reasonable predictions about the future). In one particular embodiment, the data mining techniques utilize known decision trees and classification algorithms, such as Naïve Bayes, neural network, and/or logistic regression algorithms. The predictive scheduling is based upon one or more "predicted attributes." Predicted attributes can be, for example, the shortest duration for procedure (e.g., based on one or more of the technician, location, equipment, exam, sex of patient, age of patient, and/or diagnosis coding associated with patient), the highest re-imbursement rate, the highest utilization by equipment, and/or any other predictable value within the database of the system.

In accordance with one embodiment of the present invention, the predictive scheduling system generates one or more predictive models for each classification algorithm employed. These prediction models are then used as inputs to the scheduling prediction. The outcomes of these previous completed medical procedures allows the healthcare provider to score scheduling predictions. The actual time(s) taken to perform a particular procedure over a given period (e.g., average time to perform the procedure since first use of procedure by healthcare provider) is used by the system to predict how long it will take to perform the procedure for new patients. Thus, both healthcare provider ROI and patient satisfaction with promised timing are improved, relative to conventional scheduling systems that use hard-coded or otherwise static time estimates. Also, by using decision trees and historical data (associated with previously performed procedures), the scheduling system is self-learning (each new set of patient-procedure data becomes historical data after procedure is scheduled). As such, changes in scheduling behavior will occur naturally as the system learns over time, as each procedure is performed. As is known, a decision tree is a classification type of algorithm that is used for predictive modeling.

Thus, by using analytics to compare many (e.g., tens, hundreds, thousands, etc) of previously scheduled procedures having similar patient characteristic/procedure conditions, the scheduling system maximizes the efficiency of the resources (people and equipment) while giving the patient the best possible experience.

System Architecture

Figure 1:
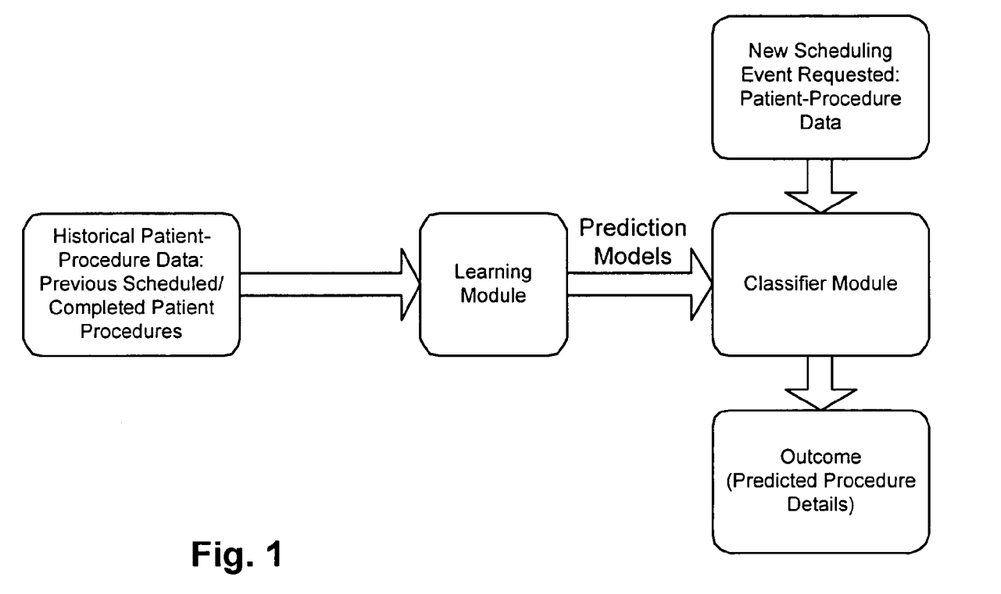
FIG. 1 is a block diagram of a predictive scheduling system for procedure medicine, configured in accordance with one embodiment of the present invention.

FIG. 1 is a block diagram of a predictive scheduling system for procedure medicine, configured in accordance with one embodiment of the present invention. The procedure could be, for example, a CT/CAT scan, MRI scan, PET scan, ultrasound, x-ray, mammogram, bone densitometry/scan, nuclear camera scan, or other such medical imaging or diagnostic procedures.

As can be seen, the system includes a learning module and a classifier module. Each of these modules can be implemented, for example, in software (e.g., C, C++, or other suitable programming language), hardware (e.g., gate level logic or ASIC), firmware (e.g., microcontroller configured with input capability for receiving historical patient-procedure data and new scheduling requests, output capability for outputting predicted procedure details, and a number of routines for carrying out learning, modeling, and classifying functions as described herein), or some combination thereof. In addition, note that the modules are shown as separate for purposes of illustration, and that other embodiments may have the various functionalities or sub-sets thereof integrated into a single module.

In operation, historical patient-procedure data is provided to the learning module, which then processes that data into a schema and uses that data to generate prediction models. The historical data comprises actual data from previously completed patient procedures, such as patient data (e.g., current symptoms, problem body site, and previous problems in that site), procedure details and attributes (e.g., body positions for best scan results, contrast agents), timing for various steps of the procedure (e.g., including registration/intake/admitting processes, as well as other timing factors such as fasting times and delays between contrast and scans), patient demographics, patient insurance data, equipment used, attending personnel (e.g., technician that performed procedure and physician that prescribed the procedure), and any other relevant information.

Multiple prediction models can be generated by the learning module, to improve the robustness of the system's predictions. In one particular embodiment, three prediction models are generated: Naïve Bayes, logistics regression, and neural network prediction models. Other prediction modeling techniques (e.g., maximum entropy), whether alone or in combination, can also be used as will be apparent in light of this disclosure. The learning module will be discussed in further detail with reference to FIGS. 3a, 3b, 3c, and 5.

The classifier module receives new scheduling event requests, and uses the prediction model(s) provided by the learning module to predict an optimal procedure that is responsive to that request. A new scheduling event request includes patient-procedure data. This data can be similar to (or a sub-set of) the type of historical patient-procedure data provided to the learning module. In one particular embodiment, the classifier module processes the new patient-procedure data through three prediction models: Naïve Bayes, logistics regression, and neural network. The classifier module then compares each of the predictions to determine if an overall prediction can be confidently made. If so, the classifier module outputs that prediction. Otherwise, no prediction is made (manual scheduling can be used). The classifier module will be discussed in further detail with reference to FIGS. 4 and 5.

Data Collection

Figure 2:
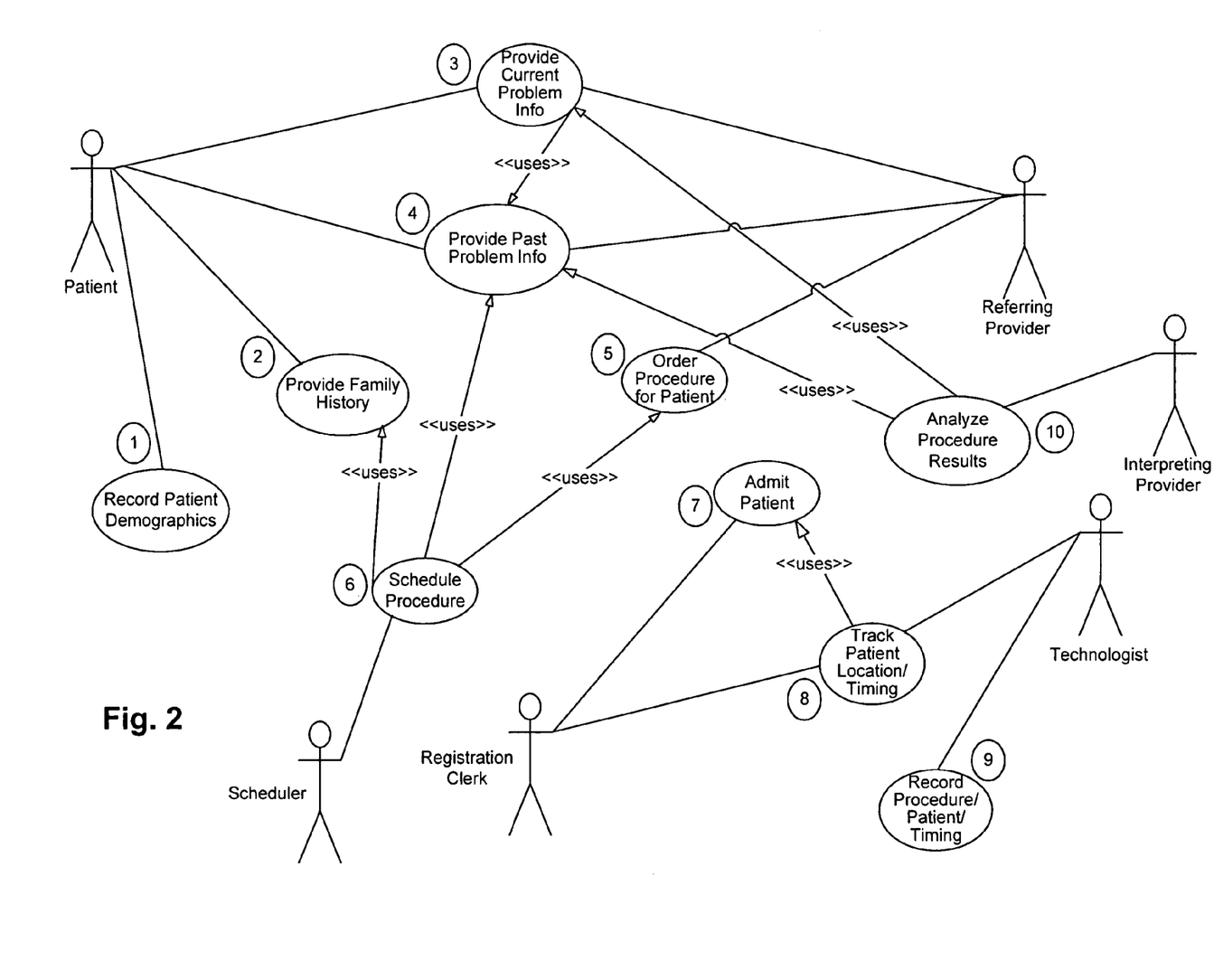
FIG. 2 illustrates a method for collecting historical patient-procedure data that can be fed to the system of FIG. 1, in accordance with one embodiment of the present invention.

FIG. 2 illustrates a method for collecting historical patient/procedure data that can be fed to the system of FIG. 1, in accordance with one embodiment of the present invention. The collected data forms the basis for the prediction model or models. It is assumed that the historical patient-procedure data from which the models are built is collected over a period of time (e.g., several weeks, months, years, decades, etc) for many patients (e.g., tens, hundreds, thousands, millions, etc).

As can be seen with reference to the UML diagram of FIG. 2, ten use cases are provided. The actors in this example use case diagram include a patient, a referring provider, a registration clerk, a scheduler, a technologist, and an interpreting provider. Note that some of these actors could actually be the same person. Likewise, there may be more than one actor.

Use case 1: Patient demographics are recorded, such as age, sex, marital status, ethnicity, height, weight, education level, address, type of work, type of insurance, and other relevant patient information.

Use case 2: Patient provides family history information, such as diabetes, heart disease, high blood pressure, high cholesterol, and other such factors that apply to the patient.

Use case 3: Referring provider or providers and patient provide information about the current problems/conditions associated with the patient (e.g., type of injury and/or symptoms).

Use case 4: Referring provider or providers and patient provide information about the patient's past problem history and ongoing status of problem history, which may or may not be related to the current problem.

Use case 5: Referring provider orders or otherwise prescribes a procedure for the patient. The procedure can be, for example, medical imaging, diagnostic testing, or laboratory work. In short, any medical procedure that requires the patient's time and/or the healthcare provider's resources can be scheduled.

Use case 6: Scheduler schedules the patient to an appropriate medical device (for carrying out the prescribed procedure) at a specific location, date, and time.

Use case 7: Patient is admitted or otherwise checks-in for the proscribed procedure.

Use case 8: Patient is tracked (physical location) within the healthcare provider's facility (e.g., hospital or clinic). Timing information is recorded.

Use case 9: Technologist performs the procedure and records the procedure duration (e.g., start and stop times), as well as general information about the patient and procedure (e.g., patient ID and body site of procedure).

Use case 10: Interpreting provider renders judgment on the results of the performed procedure.

Each of these use cases generates useful information that can be harvested and used in predictive scheduling of future patients. The data can be stored in a general database of the healthcare provider, such as a relational or object-oriented database, or other suitable storage facility.

Note the same data of use cases 1, 2, 3, 4, and 5 is also collected for new patients, who are then predictively scheduled in accordance with an embodiment of the present invention. That newly collected patient-procedure data becomes part of the historical patient-procedure data. Thus, the prediction models continue to learn as time goes on. In more detail, a new patient is processed via use cases 1 through 4, and then the referring provider orders a procedure for the patient, per use case 5. The collected data and ordered procedure can then be used as input (e.g., a new scheduling event request that includes the patient-procedure data) to the predictive scheduling system of FIG. 1. The predictive scheduling system uses this information to predictively schedule a procedure. If desired, the predictively scheduled procedure can be "overridden" by the scheduler, and use case 6 can be carried out manually. The newly collected patient-procedure data associated with the scheduled procedure is then provided to the learning module, to update the prediction models.

Learning Module

Figure 3A:
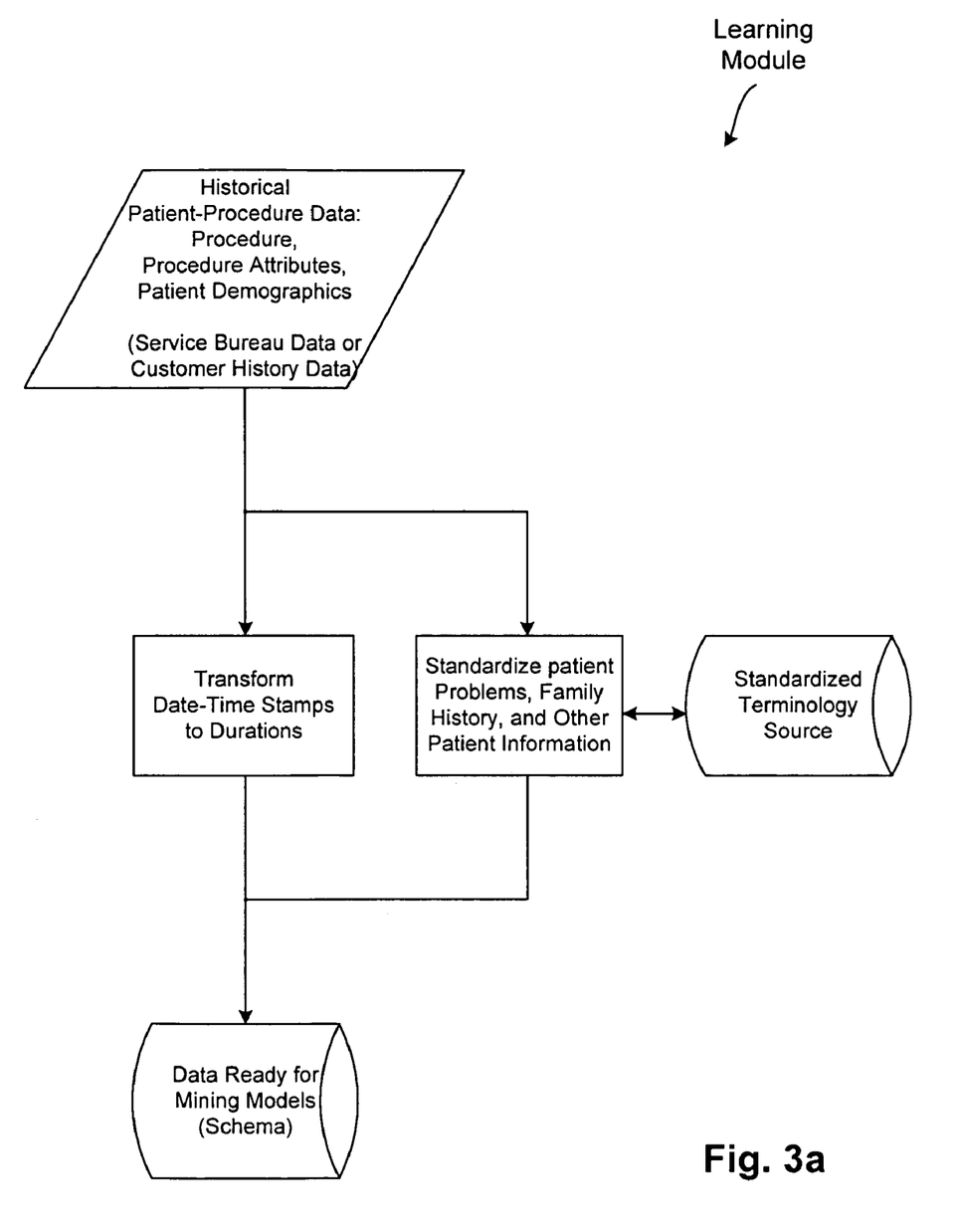
FIGS. 3a and 3b illustrate a block diagram of a learning module shown in the system of FIG. 1, configured in accordance with one embodiment of the present invention.
Figure 3B:
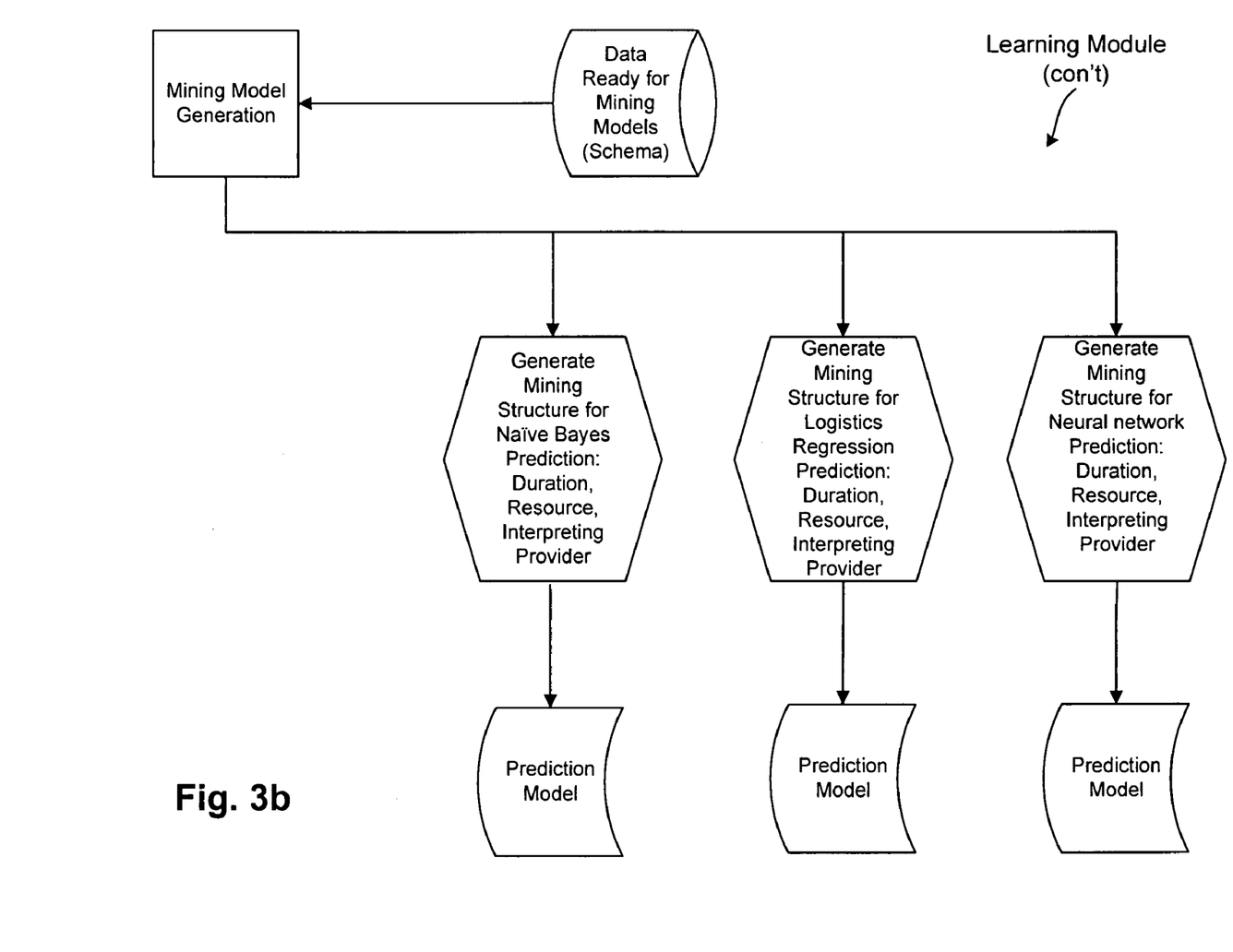

FIGS. 3a and 3b illustrate a block diagram of a learning module shown in the system of FIG. 1, configured in accordance with one embodiment of the present invention.

In particular, FIG. 3a illustrates how the learning module transforms collected historical data into a schema from which prediction models can then be built, in accordance with one embodiment of the present invention. As discussed with reference to FIG. 2, the collected historical data can be in any form and from any storage facility, such as a relational database or object-oriented data store. If the healthcare provider does not have such a historical data store (e.g., as in the case of a new imaging center or hospital), then pre-existing data can be obtained from other sources, such as from data stores of older healthcare providers. Also, by implementing various embodiments of the present invention at multiple customer sites, a robust set of service bureau data is effectively created. Such customer history data storages can be utilized for customer's not having their own historical data stores.

In any case, the learning module in this example embodiment receives the historical patient-procedure data and transforms that data. In particular, the learning module converts date-time stamps (e.g., start and stop times for steps indicated in use cases 1 through 10 of FIG. 2) to durations, and standardizes patient problems, family history, and other patient information. In general, such data transforming includes converting certain data elements to integer, ranges, and Boolean data types for mining efficiency.

For example, in one embodiment, the learning module is programmed or otherwise configured to change dates of birth to age integer values, and/or change ages to age ranges. This example learning module is also configured to change tracking dates and times into duration minutes (integer values). Other data transformations can be made according to an established code or integer association. For instance, transforming data such as body-sites can be done by associating each potential body-site with an integer number with a universally accepted healthcare terminology, such as SNOMED-CT codes. Likewise, each potential procedure codification can associated with an integer or other standard value.

In the embodiment shown in FIG. 3a, the established codes and/or standard values are stored in a standardized terminology source, such as a look-up table or fast query database that associates non-standard terms with desired standard terms (e.g., male is associated with "m" and female is associated with "f"; specific diagnostic procedure is associated with integer code 11; body-site of lower back is associated with integer code 127; procedure codification of compressed disk #2 is associated with integer code 11605). Thus, non-standard terms can be located in the standardized terminology source (e.g., using a search function), and the corresponding standard term can be then be identified. Numerous storage and look-up techniques for associating non-standard terms with desired standard terms can be used to implement the standardized terminology source. In any case, data is transformed by the learning module to be discrete and to conform to the same meaning over time, thereby enabling predictive modeling and scoring process that is consistent.

The learning module can also be configured to remove inferior input data, such as cancelled orders and/or procedures, and patient data entered in error. Also, redundancies can be eliminated by the learning module. For instance, the learning module can be configured to detect the case where a patient is in the database more than once (e.g., married and single name, where both names are associated with common social security number and/or patient ID). In such a case, the patient records can be merged. Similarly, two different patients' records can be de-merged. Also, a sub-set of a single patient's records can be removed from consideration, if so desired (e.g., where the predictive scheduling system is configured to train only on diagnostic and imaging records).

Figure 3C:
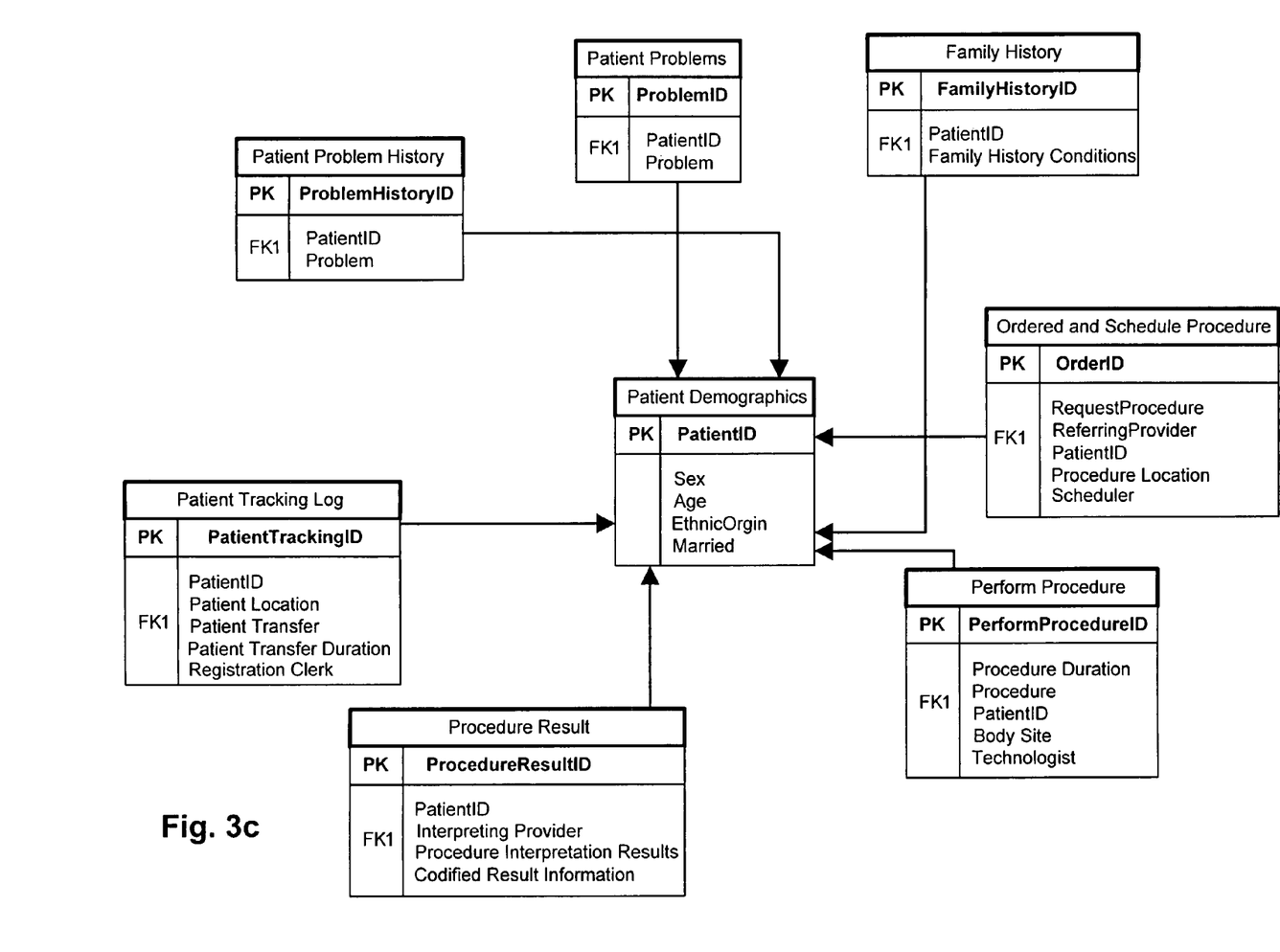
FIG. 3c illustrates a schema for the historical data collected in FIG. 2, after the data is transformed into standard values, in accordance with one embodiment of the present invention.

Once the learning module transforms the data into the desired form, that data is then stored into a schema from which prediction models can be built. FIG. 3c illustrates an example of one such schema, configured in accordance with an embodiment of the present invention. This particular schema is implemented as a star schema. As is known, a star schema is a relational database schema organized around a central fact table joined to a number of dimension tables using foreign key (e.g., FK1) references. The central fact table includes a compound primary key (e.g., PK), and in this example is the patient demographics table. Each of the other tables (patient problems, family history, ordered/scheduled procedures, perform procedure, procedure result, patient tracking log, and patient problem history tables) are dimension tables. Numerous other schema can be used, as will be apparent in light of this disclosure.

FIG. 3b illustrates how the learning module builds the prediction models from the historical data stored into the schema, in accordance with an embodiment of the present invention. As can be seen, the mining model generation performed by the learning module in this example includes using schema data of FIG. 3c (data ready for mining models) to generate each of three prediction models: Naïve Bayes prediction model, logistics regression prediction model, and a neural network prediction model. Each of these models is updated continuously as new historical patient-procedure data is received and fed to the learning module.

The prediction models can be built/updated in any order, or in parallel as shown in FIG. 3b. In this particular example, the learning module generates the mining structure for the Naïve Bayes prediction model, using durations (e.g., admitting/ check-in and/or procedure durations), resources (e.g., people and equipment), and interpreting providers (e.g., attending physician). Likewise, the learning module generates the mining structure for the logistics regression prediction model, using durations (e.g., admitting/check-in and/or procedure durations), resources (e.g., people and equipment), and interpreting providers (e.g., attending physician). Likewise, the learning module generates the mining structure for the neural network prediction model, using durations (e.g., admitting/ check-in and/or procedure durations), resources (e.g., people and equipment), and interpreting providers (e.g., attending physician). Note that additional or different data can be harvested from the schema and used to build the prediction models, as desired.

Each prediction model can be built in accordance with standard model building techniques. For instance, standard Naïve Bayes' rule can be viewed mathematically as: posterior=(likelihood*prior)/(marginal likelihood). In symbols, $P(R=r|e)=[P(e|R=r)\ P(R=r)]/P(e)$, where $P(R=r|e)$ denotes the probability that random variable R has value r given evidence e. The denominator is a normalizing constant that ensures the posterior adds up to 1, and can be computed by summing up the numerator over all possible values of R (i.e., $P(e)=P(R=0, e)+P(R=1, e)+ \ldots =sum\_r\ P(e|R=r)\ P(R=r)$). This is called the marginal likelihood (marginalize out over R), and gives the prior probability of the evidence.

Pseudo code for one example Naïve Bayes prediction model creation (using Microsoft DMX) is as follows:

CREATE MINING MODEL [PredictiveSchedulingNaive]

```
(
    PatientID LONG KEY,
    Sex TEXT DISCRETE,
    [Problem] TEXT DISCRETE,
    [Age Range] LONG DISCRETE,
    [Scheduled PROCEDURE] TEXT DISCRETE,
    [Procedure Duration] LONG DISCRETE PREDICT,
    [Exam Detail Type] TEXT DISCRETE PREDICT
)
```

Using Microsoft_Naive Bayes

As is known, DMX (Data Mining Extensions) is a language used to create and manipulate data mining objects. DMX statements can be used for creating, modifying and exploiting mining models, and DMX functions can be used to retrieve and display statistical information about the mining model. Microsoft_Naïve_Bayes is one commercially available DMX prediction model builder. In general, a Naïve Bayes calculates probabilities for each possible state of an input attribute, given each state of the predictable attribute, which can later be used to predict an outcome of the predicted attribute based on the known input attributes.

Once the prediction model structure is built, historical patient-procedure data information (e.g., successfully performed patient procedures) is applied to the model. Example Pseudo code for training/populating the prediction model (using Microsoft DMX) is as follows:

INSERT INTO PredictiveSchedulingNaive
   OPENQUERY([DataSource], SELECT*FROM [view
     Prior Procedure And Patient Information])

Similar model structure building and populating techniques can be employed to implement the logistics regression prediction model and the neural network prediction models. For instance, the learning module can generate, populate, and update the logistic regression prediction model using the Microsoft Logistic Regression algorithm. Likewise, the learning module can generate, populate, and update the neural network prediction model using the Microsoft_Neural_Network algorithm. Other prediction model generator algorithms, such as the Microsoft_Decision_Trees algorithm, can also be used.

Classifier Module

Figure 4:
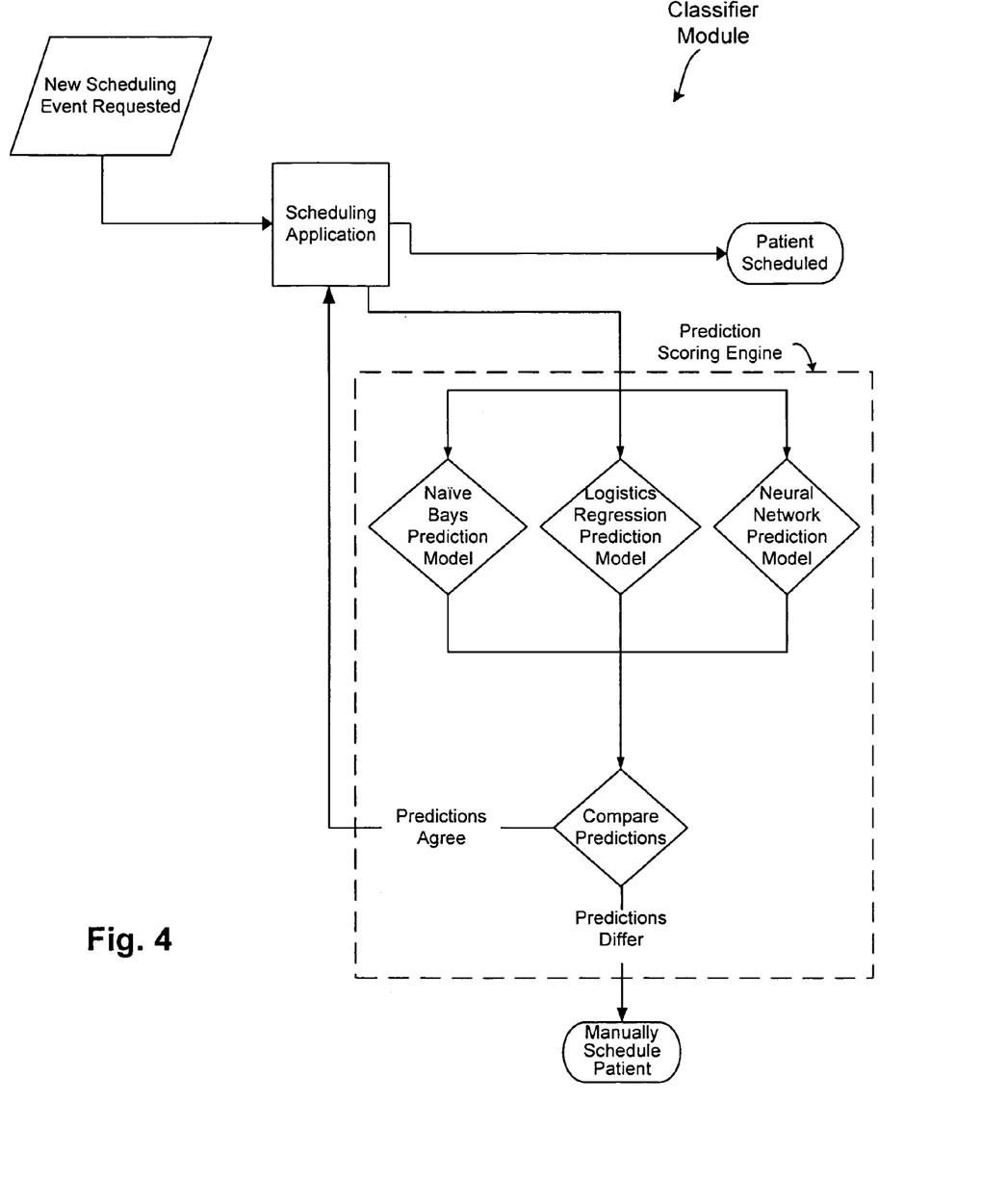
FIG. 4 is a block diagram of a classifier module shown in the system of FIG. 1, configured in accordance with one embodiment of the present invention.

FIG. 4 is a block diagram of a classifier module shown in the system of FIG. 1, configured in accordance with one embodiment of the present invention.

As can be seen, the classifier module of this example includes a scheduling application that is programmed or otherwise configured to receive new scheduling event requests, and to provide patient-procedure data from each request to a prediction scoring engine. The prediction scoring engine includes the three prediction models generated and maintained/updated by the by learning module (Naïve Bayes, logistics regression, and neural network prediction models). The prediction engine effectively operates as an analysis database in which data mining predictions are performed.

In operation, the received or "target" patient-procedure data is processed through each of the models, and given a score. A comparator module then analyzes each score from the three models to determine if the predictions are in agreement. For instance, the comparator module can be programmed or otherwise configured to determine if each score is above a predetermined threshold (after normalization of scores).

If two or three of the three predictions agree based on this determination, then a corresponding set of procedure parameters (e.g., procedure location, procedure equipment, and procedure personnel/technician) from the matched models are provided to the scheduling application, and the patient is predictively scheduled for that procedure. Otherwise, if the predictions disagree, then not prediction is made. In such a case, a manual scheduling procedure can be used.

Pseudo code for performing an example Naïve Bayes prediction model query (using Microsoft DMX) is as follows:
SELECT Predict ([Procedure Duration]) FROM Predictive-SchedulingNaive
   NATURAL PREDICTION JOIN
      (SELECT @Sex AS [SEX], @Problem AS [PROBLEM], @AgeRange AS [AGE Range], @Scheduled-Procedure AS [Scheduled Procedure])
This result of this query is then used to compare predictions as previously described. Similar prediction model query techniques can be employed for the logistics regression prediction model and the neural network prediction models (or other such prediction models), using Microsoft DMX or other suitable prediction model algorithms.

In one particular embodiment, the scheduled procedure need not match the procedure prescribed by the referring provider. For instance, the prescribed procedure may be for a chest x-ray. After the new patient-procedure data is provided to the scheduling system, the prediction models may predictively schedule a CT scan, based on the patient factors and historical patient-procedure data. Further note that the scheduled procedure may be more specific than the procedure prescribed by the referring provider. For instance, the referring provider may prescribe a CT scan of the chest. After the new patient-procedure data is provided to the scheduling system, the prediction models may predictively schedule the CT scan along with other relevant factors such as body position during scan, contrast agents, and timing factors. As previously explained, such predictive scheduling can be overridden by the referring provider if further independent analysis so dictates. In this sense, the predictive scheduling system can be used as a tool for healthcare providers, by suggesting viable procedure options that can be reviewed and confirmed by appropriate medical personnel.

Methodology

Figure 5:
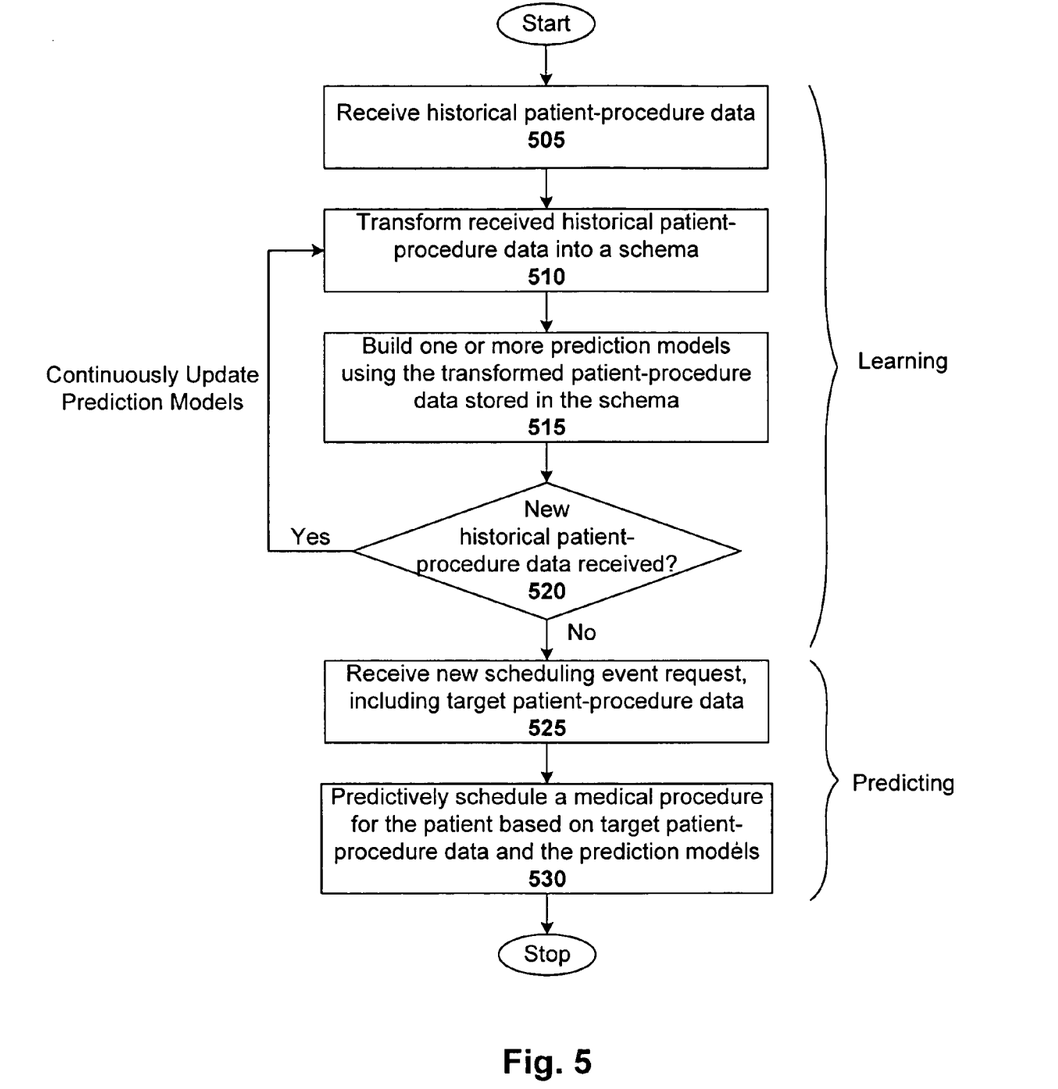
FIG. 5 illustrates a method for predictively scheduling a patient for procedure medicine, configured in accordance with one embodiment of the present invention.

FIG. 5 illustrates a method for predictively scheduling a patient for procedure medicine, configured in accordance with one embodiment of the present invention. As can be seen, the method includes a learning mode and a predicting mode. This method can be carried out, for example, by the system shown in FIG. 1, where the learning module implements the learning mode and the classification module implements the predicting mode.

The learning mode of this example method includes receiving 505 historical patient-procedure data. As previously explained, the historical patient-procedure data comprises actual data from previously completed patient procedures, such as procedure details and attributes, timing for various steps of the procedure, patient demographics, patient insurance data, equipment used, attending personnel, and any other relevant information.

The learning mode of the method continues with transforming 510 the received historical patient-procedure data into a schema (as discussed with reference to FIGS. 3a and 3c), and then building 515 one or more prediction models using the transformed patient-procedure data stored in the schema (as discussed with reference to FIG. 3b). In one such embodiment, a plurality of different prediction models are built, such as two or more of Naïve Bayes, logistics regression, neural network, maximum entropy, and decision tree prediction models.

The learning mode further includes determining 520 if new historical patient-procedure data has been received. If so, the method operates to continuously update the constructed prediction models (e.g., by repeating steps 510, 515, and 520 as needed). Thus, the learning mode can be implemented to both construct and maintain the prediction models.

In the predicting mode, the method includes receiving 525 a new scheduling event request, including target patient-procedure data. As previously explained, the target patient-procedure data includes all or a sub-set of the data types included in the historical patient-procedure data from which the prediction models are built and maintained. In one particular embodiment, the received target patient-procedure data is transformed to comply with the schema used in the learning mode (just as the historical patient-procedure data is transformed).

The predicting mode continues with predictively scheduling 530 a medical procedure for the patient, based on the target patient-procedure data and prediction models (as discussed with reference to FIG. 4). In one particular embodiment, the target patient-procedure data is processed through the prediction models to determine if procedure predictions by the models satisfy a given threshold. If so, and a quorum of predictions agree, then the patient can be scheduled for the predicted procedure. Otherwise, procedure scheduling is preformed by other means (e.g., manually). A quorum is the minimum number of model predictions that must agree to make a prediction. A quorum can be any pre-established threshold, such as a majority, a set percentage, or all of the models.

The foregoing description of the embodiments of the invention has been presented for the purposes of illustration and description. It is not intended to be exhaustive or to limit the invention to the precise form disclosed. Many modifications and variations are possible in light of this disclosure. It is intended that the scope of the invention be limited not by this detailed description, but rather by the claims appended hereto.

What is claimed is:

1. A computer-implemented method for predictively scheduling a patient for a medical event, comprising:
configuring a set of executable code in a tangible storage medium, wherein the set of executable code is executed by a processor, effectuating the following steps:
receiving historical patient-procedure data;
transforming the received historical patient-procedure data into a schema;
building one or more prediction models using the transformed patient-procedure data from the schema;
predictively scheduling the medical procedure for the patient, wherein the step of predictively scheduling the medical procedure further comprises:
processing a set of target patient procedure data in each of the plurality of prediction models and determining a score for each of the results of the processing step;
determining a majority of the scores from the plurality of prediction models agree by determining whether each score exceeds a predetermined threshold; and
predictively scheduling the medical appointment utilizing the plurality of prediction models that agree and the set of target patient-procedure data.

2. The method of claim 1, further comprising:
in response to determining new historical patient-procedure data has been received, updating the one or more prediction models.

3. The method of claim 1 wherein the step of predictively scheduling the medical procedure is preceded by:
receiving a new scheduling event request, including the target patient-procedure data.

4. The method of claim 3 wherein the target patient-procedure data is transformed to comply with the schema.

5. The method of claim 1 wherein the historical patient-procedure data comprises actual data from previously completed patient procedures, including at least one of procedure attributes, procedure durations, patient demographics, equipment used, and attending personnel.

6. The method of claim 1 wherein the one or more prediction models include at least one of Naïve Bayes, logistics regression, neural network, maximum entropy, and decision tree prediction models.

7. The method of claim 1 wherein the one or more prediction models include any of a Naïve Bayes prediction model, logistics regression prediction model, and neural network prediction model.

8. A tangible machine-readable medium encoded with instructions, that when executed by one or more processors, cause the processor to carry out a process for predictively scheduling a patient for a medical event, the process comprising:
receiving historical patient-procedure data;
transforming the received historical patient-procedure data into a schema;
building one or more prediction models using the transformed patient-procedure data from the schema;
predictively scheduling a medical procedure for the patient, wherein the step of predictively scheduling the medical procedure further comprises:
processing a set of target patient procedure data in each of the plurality of prediction models and determining a score for each of the results of the processing step;
determining a majority of the scores from the plurality of prediction models agree by determining whether each score exceeds a predetermined threshold; and
predictively scheduling the medical appointment utilizing the plurality of prediction models that agree and the set of target patient-procedure data.

9. The machine-readable medium of claim 8, the process further comprising:
in response to determining new historical patient-procedure data has been received, updating the one or more prediction models.

10. The machine-readable medium of claim 8 wherein the step of predictively scheduling a medical procedure is preceded by:
receiving a new scheduling event request, including the target patient-procedure data.

11. The machine-readable medium of claim 10 wherein the target patient-procedure data is transformed to comply with the schema.

12. The machine-readable medium of claim 8 wherein the historical patient-procedure data comprises actual data from previously completed medical procedures, including at least one of procedure attributes, procedure durations, patient demographics, equipment used, and attending personnel.

13. The machine-readable medium of claim 8 wherein the one or more prediction models include any one of Naïve Bayes, logistics regression, neural network, maximum entropy, and decision tree prediction models.

14. The machine-readable medium of claim 8 wherein the one or more prediction models include a Naïve Bayes prediction model, logistics regression prediction model, and neural network prediction model.

15. A system for predictively scheduling a patient for a medical procedure, comprising:
a tangible storage medium including a set of executable code;
a processor wherein when the processor executes the set of executable code, the following are effectuated:
a learning module, wherein the learning module transforms received historical patient-procedure data into a schema, and builds one or more prediction models using the transformed patient-procedure data from the schema; and
a classifier module, wherein the classifier module predictively schedules the medical procedure for the patient, utilizing both target patient-procedure data and the one or more prediction models;
wherein the classifier module processes a set of target patient procedure data in each of the plurality of prediction models and determines a score for each of the results of the processing step, determines a majority of the scores from the plurality of prediction models agree by determining whether each score exceeds a predetermined threshold, and predictively schedules the medical appointment utilizing the plurality of prediction models that agree and the set of target patient procedure data.

16. The system of claim 15 wherein in response to receiving new historical patient-procedure, the learning module is further configured for updating the one or more prediction models.

17. The system of claim 15 wherein the one or more prediction models include any one of a Naïve Bayes prediction model, logistics regression prediction model, and neural network prediction model.

18. A method of predictively scheduling a patient for a medical appointment, comprising:
- configuring a set of executable code in a tangible storage medium, wherein the set of executable code is executed by a processor, effectuating the following steps:
- receiving historical data relating to the medical appointment;
- transforming the received historical data into a schema;
- building a plurality of prediction models using the transformed historical data from the schema;
- processing a set of target patient procedure data in each of the plurality of prediction models and determining a score for each of the results of the processing step;
- determining a majority of the scores from the plurality of prediction models agree by determining whether each score exceeds a predetermined threshold; and
- predictively scheduling the medical appointment utilizing the plurality of prediction models that agree and the set of target patient-procedure data.

19. The method of claim 18 wherein the historical data comprises data from previously completed medical appointments, including at least one of medical procedure attributes, appointment durations, patient demographics, equipment used and attending personnel.

20. The method of claim 18 wherein the one or more prediction models include at least one of Naïve Bayes, logical regression, neuro network, maximum entropy, and decision tree prediction models.

21. The method of claim 18 wherein the steps of predictive scheduling the medical appointment is preceded by receiving a new scheduling event request, the new scheduling event request including target patient-procedure data for the medical appointment to be scheduled, wherein the medical appointment is predictively scheduled based upon the target patient-procedure data.

22. The method of claim 18 wherein the historical data includes actual data from previously completed medical appointments similar to the medical appointment being scheduled.

* * * * *